United States Patent
Farrell et al.

(10) Patent No.: US 12,049,617 B2
(45) Date of Patent: Jul. 30, 2024

(54) OPTIMIZATION OF C-8 STEROL ISOMERIZATION

(71) Applicant: DSM IP Assets B.V., Heerlen (NL)

(72) Inventors: Christopher Mark Farrell, Columbia, MD (US); Lisa Ann Laprade, Columbia, MD (US); Otto Martin Lehmann, Kaiseraugst (CH); Joshua Trueheart, Columbia, MD (US); Bastien Jean Wolfgang Chevreux, Kaiseraugst (CH)

(73) Assignee: DSM IP Assets B.V., Heerlen (NL)

( * ) Notice: Subject to any disclaimer, the term of this patent is extended or adjusted under 35 U.S.C. 154(b) by 834 days.

(21) Appl. No.: 17/050,626

(22) PCT Filed: May 21, 2019

(86) PCT No.: PCT/EP2019/063080
§ 371 (c)(1),
(2) Date: Oct. 26, 2020

(87) PCT Pub. No.: WO2019/224190
PCT Pub. Date: Nov. 28, 2019

(65) Prior Publication Data
US 2021/0238539 A1 Aug. 5, 2021

(30) Foreign Application Priority Data
May 22, 2018 (CH) .................................... 00626/18

(51) Int. Cl.
*C12N 1/16* (2006.01)
*C12N 9/90* (2006.01)
*C12P 33/00* (2006.01)

(52) U.S. Cl.
CPC .................. *C12N 1/16* (2013.01); *C12N 9/90* (2013.01); *C12P 33/00* (2013.01)

(58) Field of Classification Search
CPC .............. C12N 1/16; C12N 9/90; C12P 33/00
See application file for complete search history.

(56) References Cited

U.S. PATENT DOCUMENTS 7,608,421 B2  10/2009  Lang et al.

FOREIGN PATENT DOCUMENTS

| WO | 03/064650 | 8/2003 |
| WO | 2011/067144 | 6/2011 |
| WO | 2017/108799 | 6/2017 |

OTHER PUBLICATIONS

International Search Report for PCT/EP2019/063080 dated Sep. 4, 2019, 5 pages, with English Translation.
Written Opinion of the ISA for PCT/EP2019/063080 dated Sep. 4, 2019, 6 pages, with English Translation.
Souza et al., "A stable yeast strain efficiently producing cholesterol instead of ergosterol is functional for tryptophan uptake, but not weak organic acid resistance", Metabolic Engineering, Jun. 14, 2011, vol. 13, No. 5, XP028274823, pp. 555-569 (15 total pages).
Sambroook, "Molecular Cloning, A Laboratory Manual", Second Edition, 1989, table of contents (30 total pages).
Rice et al., "EMBOSS: The European Molecular Biology Open Software Suite", The European Molecular Biology Open Software Suite, Trends in Genetics, Jun. 2000, vol. 16, No. 6, pp. 276-277 (2 total pages).
Ausubel et al., "Current Protocols in Molecular Biology", Nov. 1988, table of contents (3 total pages).
Needleman et al., "A General Method Applicable to the Search for Similarities in the Amino Acid Sequence of Two Proteins", Journal of Molecular Biology, Mar. 28, 1970, vol. 48, No. 3, pp. 443-453 (11 total pages).
Kamper et al, *Insights from the genome of the biotrophic fungal plant pathogen Ustilago maydis*, NCBI Reference Sequence: XP 011387854.1, Nature 444 (7115), 97-101 (2006), Title, Authors, etc. only (2 pages.
Zhang et al., Effects of Post-squalene Genes on the Synthesis of 7-Dehydrochlesterol in the Artificial *Saccharomyces cerevisiae*; *China Biotechnology* 36(6) 39-50 (2016).

*Primary Examiner* — Barbara P Badio
(74) *Attorney, Agent, or Firm* — Nixon & Vanderhye, PC

(57) ABSTRACT

The present invention is related to an improved method for production of 7-dehydrocholesterol (7-DHC), an important intermediate towards biotechnological production of vitamin D3 or derivatives/metabolites thereof. The invention features modified yeast strains expressing enzymes having improved C-8 sterol isomerase activity leading to increased ratios of 7-DHC in the sterol mix.

11 Claims, No Drawings

Specification includes a Sequence Listing.

OPTIMIZATION OF C-8 STEROL ISOMERIZATION

CROSS-REFERENCE TO RELATED APPLICATIONS

This application is the U.S. national phase of International Application No. PCT/EP2019/063080 filed May 21, 2019 which designated the U.S. and claims priority to CH 00626/18 filed May 22, 2018, the entire contents of each of which are hereby incorporated by reference.

REFERENCE TO SEQUENCE LISTING SUBMITTED ELECTRONICALLY

The content of the electronically submitted sequence listing (Name: 4662-4078_Sequence_Listing.txt; Size: 29 kilobytes) filed with the application is incorporated herein by reference in its entirety.

The present invention is related to an improved method for production of 7-dehydrocholesterol (7-DHC), an important intermediate towards biotechnological production of vitamin D3 or derivatives/metabolites thereof. The invention features modified host strains expressing enzymes having improved C-8 sterol isomerase activity and their use in a process for production of vitamin D3 or derivatives and/or metabolites thereof.

Vitamin D3 (also known as cholecalciferol or calciol) can be synthesized in the skin of mammals from provitamin D3 (also known as 7-dehydrocholesterol or 7-DHC) which is the product of cholesterol biosynthesis upon exposure to UV light, whereby 7-DHC is photochemically converted into provitamin D3, which isomerizes at body temperature to the biologically active form vitamin D3. In the liver, vitamin D3 is converted to the biologically inactive 25-hydroxyvitamin D3 (also known as calcidiol, calcifediol, 25-hydroxycholecalciferol, 25-OH-D3 or HyD), which is the major circulating form of vitamin D3. Further hydroxylation occurs in the kidney.

For industrial production of vitamin D3, both chemical and biotechnological synthesis is (in principle) available. Chemical synthesis starts with cholesterol isolated from e.g. wool fat which is dehydrogenated into 7-DHC, an important intermediate in both chemical and biotechnological synthesis. Through exposure by UV-light and further purification/extraction steps 7-DHC is converted into vitamin D3. Modified yeast stains can be used for biosynthesis of 7-DHC, wherein acetyl-CoA is converted in a multi-step enzymatic process into 7-DHC. Said enzymatic conversion takes place in the endoplasmatic reticulum of the yeast. Excessive amounts of sterols, including 7-DHC and precursors thereof, not required in cellular membranes, are toxic to the yeast and are thus stored as steryl esters into intracellular organelles (so-called lipid bodies) from which they can be further isolated. The equilibrium between free sterols and those stored in the lipid bodies (mainly in the form of steryl esters) is triggered via the action of several proteins (enzymes), including action of sterol acyltransferases.

Due to the unspecific action of said sterol acyltransferase enzymes, the steryl ester pool which is stored within the lipid bodies is relatively diverse, including but not limited to e.g. esters of ergosterol, zymosterol, lanosterol, lathosterol, cholesta-5,7,24(25)-trienol, cholesta-8-enol, or 7-DHC. Only 7-DHC can be further processed into vitamin D3.

Thus, it is an ongoing task to generate host cells, such as yeast capable of producing sterols, with high productivity/specificity for 7-DHC and/or reduced accumulation of side-products/intermediates including zymosterol, lanosterol or lathosterol, in particular esters of such intermediates stored in the lipid bodies.

Surprisingly, we now found that the productivity of 7-DHC in a host cell, in particular the ratio of 7-DHC to cholesta-8-enol, can be shifted towards 7-DHC via modification of C-8 sterol isomerase activity within the host cell, i.e. expression of heterologous enzymes having C-8 sterol isomerase activity, which leads to higher productivity of the host cell towards 7-DHC as important intermediate in vitamin D3 production.

Thus, the present invention is directed to the use of an enzyme having C-8 sterol isomerase activity in a process for production of 7-DHC, said polypeptide having at least 41%, such as e.g. at least 44, 45, 48, 49, 53, 56, 60, 70, 80, 90, 92, 95, 98 or up to 100% identity to SEQ ID NO:6 being (heterologous) expressed in a suitable host cell for production of 7-DHC, wherein the ratio of 7-DHC to side-products including cholesta-8-enol is increased by at least 2-fold compared to a non-modified host cell.

The polypeptide according to SEQ ID NO:6, showing C-8 sterol isomerase activity, which might be encoded by the polynucleotide according to SEQ ID NO:2, has been isolated from *Ustilago maydis*.

The terms "C-8 sterol isomerase", "delta 8,7-isomerase", "enzyme having C-8 sterol isomerase", "isomerase" or "ERG2-homolog" are used interchangeably herein and refer to enzymes which are capable of catalyzing the conversion of cholesta-8-enol into cholesta-7-enol and/or zymosterol into cholesta-7,24-dienol. The enzymes defined herein are homologs of the *Saccharomyces cerevisiae* ERG2 (polypeptide sequence derived from UniProtKB-P32352) according to SEQ ID NO:5, which might be encoded by a polynucleotide according to SEQ ID NO:1.

The terms "conversion", "enzymatic conversion", or "isomerization" in connection with enzymatic catalysis of e.g. cholesta-8-enol to cholesta-7-enol (lathosterol) and/or zymosterol to cholesta-7,24-dienol are used interchangeably herein and refer to the action of C-8 sterol isomerase as defined herein and known in the art.

The isomerase might be used in an isolated form (e.g. in a cell-free system) or might be introduced and expressed as heterologous enzyme or extra-copies of endogenous enzymes in a suitable host cell. Thus, a suitable host cell, expresses one, two or more copies of isomerase enzymes as defined herein, leading to an increase in 7-DHC and/or improved ratio of 7-DHC compared to cholesta-8-enol, said host cell being referred to herein as genetically modified host cell. A genetically non-modified or non-modified host cell referred herein is the respective host cell carrying only the endogenous C-8 sterol isomerase activity expressed by the endogenous ERG2 gene.

As used herein, the terms "zymosterol", "lanosterol", "lathosterol", "cholesta-5,8,24(25)-trienol", "cholesta-5,7,24(25)-trienol", or "7-DHC" specifying vitamin D3 intermediates include both the free form and the ester form of said compounds. As used herein, a sterol mix contains 7-DHC and "side-products" or intermediates, including but not limited to zymosterol, lanosterol, lathosterol, cholesta-8-enol, cholesta-5,8,24(25)-trienol, or cholesta-5,7,24(25)-trienol.

As used herein, a "cholesterol-producing yeast" cannot produce ergosterol anymore but cholesterol products, including, but not limited to cholesta-5,7,24(25)-trienol, cholesta-5,8,24(25)-trienol, cholesta-7,24(25)-dienol, cholesta-8-enol, 7-DHC or zymosterol. Particularly, this might be achieved via introduction of erg5erg6 double-knock out.

Suitable isomerases as defined herein might be obtainable from different sources, such as e.g. plants, animals, including humans, algae, fungi, including yeast, or bacteria, preferably from fungi, particularly selected from the group consisting of *Saccharomyces, Yarrowia, Kluyveromyces, Schizosaccharomyces, Pichia, Candida, Penicillium, Aspergillus, Cryptococcus, Magneporte, Metarhizium*, and *Ustilago*, more preferably selected from *S. cerevisiae, Y. lipolytica, K. lactis, Schizosaccharomyces pombe, P. pastoris, C. albicans, P. roqueforti, A. nidulans, C. neoformans, Magneporte oryzae, Metarhizium acridum*, or *U. maydis*, most preferably from *U. maydis*.

In a preferred embodiment, the enzyme having C-8 sterol isomerase activity is obtainable from *Ustilago*, particularly *Ustilago maydis*, such as e.g. a protein encoded by a polynucleotide according to SEQ ID NO:2, more preferably said protein is a polypeptide according to SEQ ID NO:6 (polypeptide sequence derived from UniProtKB-P32360).

In another embodiment, the enzyme having C-8 sterol isomerase activity is obtainable from *Candida*, particularly *Candida albicans*, such as e.g. a protein encoded by a polynucleotide according to SEQ ID NO:3, more preferably said protein is a polypeptide according to SEQ ID NO:7 (polypeptide sequence derived from UniProtKB-C4YFH6).

In a further embodiment, the enzyme having C-8 sterol isomerase activity is obtainable from *Schizosaccharomyces*, particularly *Schizosaccharomyces pombe*, such as e.g. a protein encoded by a polynucleotide according to SEQ ID NO:4, more preferably said protein is a polypeptide according to SEQ ID NO:8 (polypeptide sequence derived from UniProtKB-P87113).

In one embodiment, the enzyme having C-8 sterol isomerase activity is obtainable from *Saccharomyces*, particularly *Saccharomyces cerevisiae*, such as e.g. a protein encoded by a polynucleotide according to SEQ ID NO:1, more preferably said protein is a polypeptide according to SEQ ID NO:5 (polypeptide sequence derived from UniProtKB-P32352), said enzyme being expressed additionally and/or as replacement of the endogenous ERG2 when using *S. cerevisiae* as host.

Further embodiments include a process for production of 7-DHC in a suitable host cell, e.g. yeast cell, particularly cholesterol-producing yeast cell, wherein an ERG2-homolog from *Y. lipolytica* (e.g. polypeptide sequences derived from UniProtKB-Q6CEA6 or Q6C3U4), *K. lactis* (e.g. polypeptide sequence derived from UniProtKB-Q6CL22), *P. pastoris* (e.g. polypeptide sequences derived from UniProtKB-F2QZY6 or C4R749), *P. roqueforti* (e.g. polypeptide sequence derived from UniProtKB-W6PX20), *A. nidulans* (e.g. polypeptide sequence derived from UniProtKB-C8VT80), *C. neoformans* (e.g. polypeptide sequence derived from UniProtKB-J9VMS8), *Magnaporthe oryzae* (e.g. polypeptide sequence derived from UniProtKB-P33281), or *Metarhizium acridum* (e.g. polypeptide sequence derived from UniProtKB-E9EHP6) is expressed in a suitable cholesterol-producing yeast cell under suitable conditions as described herein.

Based on the sequences as disclosed herein and on the improved accumulation of 7-DHC and/or reduction of cholesta-8-enol in the sterol mix, i.e. leading to at least 80%, such as 85, 90, 95, 98 or even 100% 7-DHC present in the sterol mix, one could easily deduce further suitable genes encoding polypeptides having C-8 sterol isomerase activity as defined herein which could be used for the isomerization of C-8 sterols as defined herein, particularly zymosterol and cholesta-8-enol. Thus, the present invention is directed to a method for identification of novel isomerases, wherein a polypeptide with at least 43%, such as e.g. at least 47, 50, 56, 60, 70, 75, 80, 90, 92, 95, 98 or up to 100% identity to *Saccharomyces cerevisiae* ERG2 (SEQ ID NO:5), is used as a probe in a screening process for new C-8 sterol isomerases, with preference for production of 7-DHC over cholesta-8-enol, leading to at least 80% 7-DHC in the sterol mix produced by a suitable host strain. Any polypeptide having C-8 sterol isomerase activity and disclosed herein might be used for production of 7-DHC, as long as the isomerizing action results in at least about 80% 7-DHC in the sterol mix, based on the total amount of produced sterols and/or increased ratio of 7-DHC to cholesta-8-enol.

The present invention is particularly directed to the use of such novel isomerase enzymes, particularly heterologous enzymes, in a process for production of 7-DHC, wherein the production of side-products in the sterol mix including cholesta-8-enol, zymosterol, lathosterol or lanosterol is reduced to about 20% or less, such as 15, 10, 5, 3% or less based on the total amounts of sterols, by the action of said isomerases, as defined herein, particularly wherein the amount of cholesta-8-enol towards the amount of 7-DHC is reduced. The process might be performed with a suitable cholesterol-producing yeast cell expressing said heterologous isomerases, preferably wherein the genes encoding said enzymes are heterologous expressed, i.e. introduced into said host cells. 7-DHC can be further converted into vitamin D3 by the action of (known) suitable chemical or biotechnological mechanisms.

The terms "sequence identity", "% identity" are used interchangeably herein. For the purpose of this invention, it is defined here that in order to determine the percentage of sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/bases or amino acids. The sequence identity is the percentage of identical matches between the two sequences over the reported aligned region. The percent sequence identity between two amino acid sequences or between two nucleotide sequences may be determined using the Needleman and Wunsch algorithm for the alignment of two sequences (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, Longden and Bleasby, Trends in Genetics 16, (6) pp276-277, emboss.bioinformatics.nl). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the invention is calculated as follows: number of corresponding positions in the alignment showing an identical amino acid or identical nucleotide in both sequences divided by the total length of the alignment after subtraction of the total number of gaps in the alignment. The identity as defined herein can be obtained from NEEDLE by using the NOBRIEF option and is labeled in the output of the program as "longest identity". If both amino acid sequences which are compared do not differ in any of their amino acids, they are identical or have 100% identity. With regards to enzymes originated from plants as defined herein, the skilled person is aware of the fact that plant-derived enzymes might contain a chloroplast targeting signal which is to be cleaved via specific enzymes, such as e.g. chloroplast processing enzymes (CPEs).

The ERG2 enzymes/homologs, as defined herein also encompass enzymes carrying amino acid substitution(s) which do not alter enzyme activity, i.e. which show the same properties with respect to the wild-type enzyme and catalyze the isomerization of C-8 sterols, leading to a percentage of at least 80% 7-DHC (with reduction of cholesta-8-enol towards 7-DHC) in the sterol mix. Such mutations are also called "silent mutations", which do not alter the (enzymatic) activity of the enzymes as described herein.

Depending on the host cell the polynucleotides as defined herein involved in C-8 sterol isomerization might be optimized for expression in the respective host cell. The skilled person knows how to generate such modified polynucleotides. It is understood that the polynucleotides as defined herein also encompass such host-optimized nucleic acid molecules as long as they still express the polypeptide with the respective activities as defined herein. Examples of such host-optimized ERG2 homologs are shown in e.g. SEQ ID NOs:9, 10, and 11.

Thus, in one embodiment, the present invention is directed to a host cell comprising polynucleotides encoding (heterologous) ERG2 homologs as defined herein which are optimized for expression in said host cell, with no impact on growth or expression pattern of the host cell or the enzymes. Particularly, the yeast, e.g. the cholesterol-producing yeast cell, is selected from *Saccharomyces*, such as e.g. *Saccharomyces cerevisiae*, wherein one, two or more copies of the polynucleotides encoding the ERG2 enzymes as defined herein are selected from polynucleotides with at least 52%, such as e.g. 54, 60, 70, 80, 85, 90, 92, 97 or up to 100% identity to SEQ ID NOs:9, including polynucleotides encoding the polypeptides according to SEQ ID NO:5, 6, 7, 8.

A nucleic acid molecule according to the invention may comprise only a portion or a fragment of the nucleic acid sequence provided by the present invention, such as for instance the sequences shown in SEQ ID NO:1, 2, 3, 4, 9, 10 or 11, for example a fragment which may be used as a probe or primer or a fragment encoding a portion of ERG2 homolog as defined herein. The probe/primer typically comprises substantially purified oligonucleotides which typically comprise a region of nucleotide sequence that hybridizes preferably under highly stringent conditions to at least about 12 or 15, preferably about 18 or 20, more preferably about 22 or 25, even more preferably about 30, 35, 40, 45, 50, 55, 60, 65, or 75 or more consecutive nucleotides of a nucleotide sequence according to SEQ ID NO: 1, 2, 3, 4, 9, 10 or 11 or fragments or derivatives thereof.

A preferred, non-limiting example of such hybridization conditions are hybridization in 6× sodium chloride/sodium citrate (SSC) at about 45° C., followed by one or more washes in 1×SSC, 0.1% SDS at 50° C., preferably at 55° C., more preferably at 60° C. and even more preferably at 65° C.

Highly stringent conditions include, for example, 2 h to 4 days incubation at 42° C. using a digoxigenin (DIG)-labeled DNA probe (prepared by using a DIG labeling system; Roche Diagnostics GmbH, 68298 Mannheim, Germany) in a solution such as DigEasyHyb solution (Roche Diagnostics GmbH) with or without 100 µg/ml salmon sperm DNA, or a solution comprising 50% formamide, 5×SSC (150 mM NaCl, 15 mM trisodium citrate), 0.02% sodium dodecyl sulfate, 0.1% N-lauroylsarcosine, and 2% blocking reagent (Roche Diagnostics GmbH), followed by washing the filters twice for 5 to 15 minutes in 2×SSC and 0.1% SDS at room temperature and then washing twice for 15-30 minutes in 0.5×SSC and 0.1% SDS or 0.1×SSC and 0.1% SDS at 65-68° C.

The present invention is particularly directed to the use of heterologous enzymes having C-8 sterol isomerase activity as defined herein in a process for production of 7-DHC, an intermediate for vitamin D3. Preferably, the modified enzymes of the present invention are introduced and/or expressed in a suitable host cell, such as yeast, in particular a cholesterol-producing yeast cell, such as selected from *Saccharomyces cerevisiae*, *Schizosaccharomyces* spp., *Pichia* spp., *Kluyveromyces* spp., *Hansenula* spp. or *Yarrowia lipolytica*, preferably *S. cerevisiae*. The modified host is used for production of 7-DHC, which might be further converted into vitamin D3 and/or 25-hydroxyvitamin D3.

A suitable host cell might be further modified to further increase production of 7-DHC, an important intermediate towards biosynthesis of vitamin D3, and/or reduce accumulation of side-products.

Thus, in one embodiment the invention is directed to a yeast strain having modified C-8 activity and furthermore wherein ERG5 and ERG6 are inactivated. The yeast cell might be further modified via expression of a heterologous enzyme having C24-reductase activity, particularly selected from EC 1.3.1.72, such as a heterologous C24-reductase that is active on cholesta-7,24-dienol, zymosterol, or trienol (e.g. cholesta-5,7,25-trienol), preferably a plant or vertebrate sterol Δ24-reductase, more preferably from vertebrate source, even more preferably from human, pig, dog, mouse, rat, horse, *Danio rerio* or any known source, as long as it can be expressed within said yeast cell. Most preferably, the sterol Δ24-reductase is selected from *Danio rerio*, rat or human. The sequences expressing said sterol Δ24-reductase enzymes are publicly available, including but not limited to polypeptide sequences derived from UniProtKB/Swiss-Prot reference Q15392, Q60HC5, Q8VCH6, Q5BQE6, Q39085 or P93472 (see e.g. WO2003064650).

In another embodiment, the host cell according to the present invention might be further modified via introduction of homologs of endogenous enzymes involved in biosynthesis of 7-DHC, such as e.g. C5-sterol desaturase (ERG3), resulting in increased specificity and/or productivity of 7-DHC with reduced accumulation of side-products or vitamin D3 intermediates, including but not limited to zymosterol, lanosterol and/or lathosterol. Preferably, the modified host cell as defined herein comprises a heterologous ERG3, wherein the ERG3 is preferably selected from *Pichia pastoris* (polypeptide sequence derived from UniProtKB-C4QY87; SEQ ID NO:14) or *Schizosaccharomyces pombe* (polypeptide sequence derived from UniProtKB-O94457).

In a further embodiment, the host cell according to the present invention might be further modified in the sterol acyltransferase activity, particularly activity of sterol acyltransferase isoform Are1p and/or Are2p, particularly Are1p, comprising one of more amino acid substitution(s) at (a) position(s) corresponding to residues selected from 592 and/or 595 in the polypeptide according to SEQ ID NO:12.

In a particular embodiment, the invention relates to a process for improving a yeast cell towards production of 7-DHC, wherein a modified host cell as defined herein, i.e. expressing an ERG2 homolog as defined herein, e.g. via introduction of one, two or more copies of isomerase enzymes as defined herein, in particular cholesterol-producing yeast cell, preferably a yeast cell in which ERG5 and ERG6 are inactivated and wherein optionally a heterologous enzyme having C-24-reductase activity as defined herein is expressed and/or wherein ARE1 and/or ARE1 are modified as described herein and/or wherein optionally homologs of ERG3 are expressed, wherein the host cell is improved such that the percentage of 7-DHC in the total amount of sterol produced by said host cell is increased to about at least 80%, in particular wherein the ratio of 7-DHC to side-products including cholesta-8-enol is increased by at least 1.1-fold and as compared to a non-modified yeast strain as defined herein, i.e. expressing only the wild-type (endogenous) ERG2 activity.

In a particular embodiment, the invention relates to a process for improving a yeast cell towards production of 7-DHC, wherein in particular a cholesterol-producing yeast cell, such as a yeast cell in which ERG5 and ERG6 are inactivated and wherein optionally a heterologous enzyme having C-24-reductase activity as defined herein is expressed, said yeast cell expressing an ERG2 homolog as defined herein, e.g. via introduction of one, two or more copies of desaturase enzymes as defined herein, wherein the yeast cell is improved such that the percentage of 7-DHC, in the total amount of sterol produced by said yeast is increased to at least about 80%, such as e.g. 85, 90, 92, 95, 97 or even 100%, and the percentage of side-products in the sterol mix including cholesta-7-enol, lathosterol and/or cholesta-8-enol and/or zymosterol, is reduced to about 20% or less based on the total amounts of sterols, i.e. a reduction of cholesta-7-enol, lathosterol and/or cholesta-8-enol and/or zymosterol in the range of at least about 20% based on the total amounts of sterols and compared to a non-modified yeast strain expressing the wild-type (endogenous) ERG2 activity.

In one aspect, the present invention is directed to a process for production of a sterol mix comprising 7-DHC and cholesta-8-enol in a cholesterol-producing yeast cell, wherein the ratio of 7-DHC to cholesta-8-enol in the sterol mix is increased by at least about 2.4-times, such as e.g. 2.5, 2.8, 4, 4.5, 5-times, said cholesterol-producing yeast cell expressing a heterologous isomerase as defined herein, i.e. a polypeptide with at least 41%, such as e.g. at least 44, 45, 48, 49, 53, 56, 60, 70, 80, 90, 92, 95, 98 or up to 100% identity to SEQ ID NO:2, more preferably expressed by the respective codon-optimized polynucleotides as defined herein, such as preferably obtainable from *Ustilago maydis*, *Candida albicans*, *Schizosaccharomyces pombe*, or *Saccharomyces cerevisiae*, such as preferably obtainable from *Ustilago maydis* or *Saccharomyces cerevisiae*.

In one aspect, the present invention is directed to a process for production of a sterol mix comprising 7-DHC and a mix of cholesta-7-enol (lathosterol) and/or lanosterol in a cholesterol-producing yeast cell, wherein the ratio of 7-DHC to lano-/lathosterol in the sterol mix is increased by at least about 1.1-times, such as at least about 1.3-times, said cholesterol-producing yeast cell expressing a (heterologous) isomerase as defined herein, i.e. a polypeptide with at least 41%, such as e.g. at least 44, 45, 48, 49, 53, 56, 60, 70, 80, 90, 92, 95, 98 or up to 100% identity to SEQ ID NO:6, more preferably expressed by the respective codon-optimized polynucleotides as defined herein, such as preferably obtainable from *Ustilago maydis* or *Schizosaccharomyces pombe*, particularly from *Ustilago maydis*.

In a further aspect, the present invention is directed to a process for production of a sterol mix comprising 7-DHC and zymosterol in a cholesterol-producing yeast cell, wherein the ratio of 7-DHC to zymosterol in the sterol mix is increased by at least about 1.2-times, said cholesterol-producing yeast cell expressing a (heterologous) isomerase as defined herein, i.e. a polypeptide with at least 41%, such as e.g. at least 44, 45, 48, 49, 53, 56, 60, 70, 80, 90, 92, 95, 98 or up to 100% identity to SEQ ID NO:6, more preferably expressed by the respective codon-optimized polynucleotides as defined herein, such as preferably obtainable from *Ustilago maydis*.

In a particular embodiment, the present invention is directed to a process for production of a sterol mix comprising 7-DHC, zymosterol, cholesta-8-enol, lano- or lathosterol in a cholesterol-producing yeast cell, wherein the percentage of 7-DHC is increased by at least about 5, 8, 10, 20, 30% compared to either zymosterol, cholesta-8-enol, and lano- or lathosterol based on the total amount of sterols, said cholesterol-producing yeast cell expressing a heterologous isomerase as defined herein, i.e. a polypeptide with at least 41%, such as e.g. at least 44, 45, 48, 49, 53, 56, 60, 70, 80, 90, 92, 95, 98 or up to 100% identity to SEQ ID NO:6, more preferably expressed by the respective codon-optimized polynucleotides as defined herein, such as preferably obtainable from *Ustilago maydis*.

As used herein, an increase in the percentage of 7-DHC within a sterol mix is defined as the amount of 7-DHC produced by a host cell expressing a heterologous polypeptide having isomerase activity as defined herein compared to a host cell with only expressing the endogenous C-8 sterol isomerase, such as e.g. expressed by ERG2. When using said host cell, e.g. yeast, in particular cholesterol-producing yeast cell, in a sterol production process, the percentage of 7-DHC can be increased to about 80% or more, preferably such as 85, 90, 92, 95, 97 or up to 100% based on the total amount of sterols and to about up to 4.5-times in comparison to the percentage of a cholesta-8-enol within the total amount of sterols produced by said host cell. As used herein, "expression of an ERG2-homolog" includes the expression of extra-copies of endogenous ERG2 polypeptides, i.e. expression of two or more copies of ERG2.

In a particular embodiment, the invention is directed to a process for the production of a sterol mix wherein a yeast cells as described before is used and wherein the percentage of cholesta-8-enol and/or zymosterol and/or lanosterol and/or lathosterol present in said sterol mix is reduced, i.e. is in the range of about 2, 4, 5, 8, 10, 15, 20% or less based on the total amount of sterols, i.e. leading to higher ratio of 7-DHC in the sterol mix.

A modified host cell, which is capable of expressing the ERG2 homologs as defined herein, and further genes required for biosynthesis of vitamin D3 precursors and/or intermediates, is used in a process for production of vitamin D3 precursor 7-DHC. The modified host cell may be cultured in an aqueous medium supplemented with appropriate nutrients under aerobic or anaerobic conditions and as known by the skilled person for the respective cholesterol-producing host cells. Optionally, such cultivation is in the presence of proteins and/or co-factors involved in transfer of electrons, as known in the art. The cultivation/growth of the host cell may be conducted in batch, fed-batch, semicontinuous or continuous mode. Depending on the host cell, preferably, production of vitamin D3 and precursors thereof such as 7-DHC can vary, as it is known to the skilled person. Cultivation and isolation of 7-DHC and other intermediates in production of vitamin D3 is described in e.g. WO2011067144 or WO2017108799.

Using a host cell as described herein, the productivity/specificity of C-8 sterol isomerase activity could be shifted towards 7-DHC, leading to a ratio of at least 80% 7-DHC in the total sterols produced by said host cell, with titers of up to about 12-15 g/l 7-DHC produced after 100 h fermentation under suitable culture conditions.

The terms "ERG5" and "Erg5p" or "ERG6" and "Erg6p" are used interchangeably herein and refer to a polypeptide encoded by the respective genes erg3, erg5, and erg6.

Genes encoding ERG5, ERG6, ERG2, ERG3, ARE1, ARE2 or sterol Δ24-reductase (ERG4), cultivation and genetic engineering of the yeast cell as used herein are known and described in e.g. U.S. Pat. No. 7,608,421.

As used herein, the terms "C-24-reductase" or "Δ24-reductase" are used interchangeably herein. In yeast, this enzyme is encoded by erg4 and is active on the methyl-group of the carbon atom on position 24. Trienol, which does not exhibit such methyl-group on said position, is therefore not an acceptable substrate for the yeast ERG4.

The terms "C-5 sterol desaturase", "enzyme having C-5 sterol desaturase activity" are used interchangeably herein and refer to enzymes which are capable of catalyzing the conversion of cholesta-8-enol into cholesta-7,24-dienol and/or cholesta-7-enol into cholesta-5,7,24-trienol and/or 7-DHC. In yeast, this enzyme is encoded by erg3. A preferred ERG3 homolog to be used in a modified host cell according to the present invention is a polypeptide having at least 45%, such as e.g. at least 50, 52, 60, 70, 80, 90, 92, 95, 98 or up to 100% identity to SEQ ID NO:14 showing C-5 sterol desaturase activity which might be encoded by a polynucleotide according to SEQ ID NO:15 obtainable from *Pichia pastoris* or *Schizosaccharomyces pombe*. Particularly, 1 or more copies, such as at least 1, 2, 3, 5, of said ERG3 homolog are expressed in a modified host cell as defined herein.

As used herein, the term "specific activity" or "activity" with regards to enzymes means its catalytic activity, i.e. its ability to catalyze formation of a product from a given substrate. The specific activity defines the amount of substrate consumed and/or product produced in a given time period and per defined amount of protein at a defined temperature. Typically, specific activity is expressed in μmol substrate consumed or product formed per min per mg of protein. Typically, μmol/min is abbreviated by U (=unit). Therefore, the unit definitions for specific activity of μmol/min/(mg of protein) or U/(mg of protein) are used interchangeably throughout this document. An enzyme is active, if it performs its catalytic activity in vivo, i.e. within the host cell as defined herein or within a suitable (cell-free) system in the presence of a suitable substrate. The skilled person knows how to measure enzyme activity, such as e.g. by HPLC.

With regards to the present invention, it is understood that organisms, such as e.g. microorganisms, fungi, algae or plants also include synonyms or basonyms of such species having the same physiological properties, as defined by the International Code of Nomenclature of Prokaryotes or the International Code of Nomenclature for algae, fungi, and plants (Melbourne Code).

In particular, the present invention features the present embodiments:

(1) A cholesterol-producing yeast cell as defined herein comprising an enzyme having C8-sterol isomerase activity, said yeast cell producing a sterol mix comprising at least about 80% 7-dehydrocholesterol (7-DHC), preferably comprising at least about 82, 85, 88, 90, 92, 95, 97, 98 or up to 100% 7-DHC based on the total amount of sterols.

(2) A cholesterol-producing yeast cell as defined herein and as of (1), wherein the ratio of 7-DHC to cholesta-8-enol is in the range of 20.

(3) A cholesterol-producing yeast cell as defined herein and of (1), wherein the ratio of 7-DHC to cholesta-8-enol is increased by at least 2-fold.

(4) A cholesterol-producing yeast cell as defined herein or as of (1), (2), (3), expressing a heterologous enzyme having C8-sterol isomerase activity with at least 42%, such as e.g. at least 43, 44, 47, 48, 49, 50, 51, 52, 53, 54, 55, 56, 75, 80, 90, 92, 95, 98 or up to 100% identity to the polypeptide according to SEQ ID NO:6.

(5) A cholesterol-producing yeast cell as defined herein and as of (4) expressing a heterologous enzyme having C8-sterol isomerase activity, said enzyme being selected from the group consisting of *Saccharomyces*, such as *Saccharomyces cerevisiae*, *Yarrowia*, such as *Y. lipolytica*, *Kluyveromyces*, such as *K. lactis*, *Schizosaccharomyces*, such as *Schizosaccharomyces pombe*, *Pichia*, such as *P. pastoris*, *Candida*, such as *C. albicans*, *Penicillium*, such as *P. roqueforti*, *Aspergillus*, such as *A. nidulans*, *Cryptococcus*, such as *C. neoformans*, *Magneporte*, such as *Magneporte oryzae*, *Metarhizium*, such as *Metarhizium acridum*, and *Ustilago*, such as *Ustilago maydis*.

(6) A cholesterol-producing yeast cell as defined above and of (1), (2), (3), (4), (5), in which ERG5 and ERG6 are inactivated.

(7) A cholesterol-producing yeast cell as defined herein and as of (1), (2), (3), (4), (5), (6), wherein the yeast cell expresses a heterologous enzyme selected from EC 1.3.1.72 having sterol Δ24-reductase activity, preferably wherein the heterologous enzyme is originated from plant or vertebrate, more preferably originated from human, pig, dog, mouse, rat, horse or *Danio rerio*.

(8) A cholesterol-producing yeast cell as defined herein or as of (1), (2), (3), (4), (5), (6), (7), wherein the yeast cell expresses a heterologous enzyme having C5-desaturase activity, preferably wherein the heterologous enzyme is obtainable from *Pichia pastoris*, more preferably from a polypeptide having at least 45%, such as e.g. at least 50, 52, 60, 70, 80, 90, 92, 95, 98 or up to 100% identity to SEQ ID NO:14.

9. Use of a cholesterol-producing yeast cell as defined herein and as of (1), (2), (3), (4), (5), (6), (7), (8) for production of sterols, preferably for the production of vitamin D3 precursors, more preferably for the production of 7-DHC.

(10) Use of a cholesterol-producing yeast cell as defined herein or as of (9), wherein the 7-DHC is further converted into vitamin D3.

(11) Use as defined herein and of (9), (10), wherein the 7-DHC is further converted into 25-hydroxyvitamin D3.

(12) A process for reducing the amount of cholesta-8-enol in a sterol mix produced by a yeast cell, said process comprising expression of a heterologous enzyme having C8-sterol isomerase activity, said enzyme being selected from the group consisting of *Saccharomyces*, such as *Saccharomyces cerevisiae*, *Yarrowia*, such as *Y. lipolytica*, Kluyveromyces, such as *K. lactis*, *Schizosaccharomyces*, such as *Schizosaccharomyces pombe*, *Pichia*, such as *P. pastoris*, *Candida*, such as *C. albicans*, *Penicillium*, such as *P. roqueforti*, *Aspergillus*, such as *A. nidulans*, *Cryptococcus*, such as *C. neoformans*, *Magneporte*, such as *Magneporte oryzae*, *Metarhizium*, such as *Metarhizium acridum*, and *Ustilago*, such as *Ustilago maydis*, preferably selected from *Ustilago maydis*, *Schizosaccharomyces pombe*, *Candida albicans*, or *Saccharomyces cerevisiae*.

(13) A process for the production of a sterol mix, preferably a vitamin D3-precursor, more preferably a sterol mix with at least 80% 7-DHC, in a yeast cell comprising:
  (a) inactivation of ERG5 and ERG6,
  (b) expressing of a heterologous enzyme selected from EC 1.3.1.72 having sterol Δ24-reductase activity on cholesta-7,24-dienol, zymosterol or trienol, preferably plant or vertebrate sterol Δ24-reductase, more preferably vertebrate sterol Δ24-reductase,
  (c) expression of a heterologous enzyme having C8-sterol isomerase activity, said enzyme being selected from the group consisting of *Saccharomyces*, such as *Saccharomyces cerevisiae*, *Yarrowia*, such as *Y. lipolytica*, *Kluyveromyces*, such as *K. lactis*, *Schizosaccharomyces*, such as *Schizosaccharomyces pombe*, *Pichia*, such as *P. pastoris*, *Candida*, such as *C. albicans*, *Penicillium*, such as *P. roqueforti*, *Aspergillus*, such as *A. nidulans*, *Cryptococcus*, such as *C. neoformans*, *Magneporte*, such as *Magneporte oryzae*, *Metarhizium*, such as *Metarhizium acridum*, and *Ustilago*, such as *Ustilago maydis*, preferably selected from *Ustilago maydis*, *Schizosaccharomyces pombe*, *Candida albicans*, or *Saccharomyces cerevisiae*,
  (d) cultivating said yeast cell under conditions suitable for sterol production; wherein the ratio of 7-DHC to cholesta-8-enol present in the sterol mix is more than 8.7.

The following examples are illustrative only and are not intended to limit the scope of the invention in any way.

EXAMPLES

Example 1: General Methods, Strains and Plasmids

All basic molecular biology and DNA manipulation procedures described herein were generally performed according to Sambrook et al. (1989. Molecular Cloning: A Laboratory Manual. Cold Spring Harbor Laboratory Press: New York) or Ausubel et al. (1998. Current Protocols in Molecular Biology. Wiley: New York). Genotyps of the used *S. cerevisiae* strains and plasmids are listed in Table 1 and 2. *Saccharomyces cerevisiae* 7-DHC producing strain Y2159 was constructed as described in Example 4. All listed strains are MATα.

TABLE 1

*Saccharomyces cerevisiae* strains.

| | | |
|---|---|---|
| Y2159 | erg5Δ::PGK1p-S24R2-CYC1t-TRP1<br>erg6Δ::TDH3p-S24R1-PGK1t-URA3<br>erg4Δ::PGK1p-Scer-are1 G595D-CYC1t-LEU2<br>TDH3p-tHMG1 | See Example 4 |
| | erg5Δ::PGK1p-S24R2-CYC1t-TRP1<br>erg6Δ::TDH3p-S24R1-PGK1t-URA3<br>erg4Δ::PGK1p-Scer-are1 G595D-CYC1t-LEU2<br>TDH3p-tHMG1 INT59 :: HSP26p-*S. cerevisiae*-ERG2-TDH3t-NAT$^R$ | Targeted insertion construct at INT59 locus |
| | erg5Δ::PGK1p-S24R2-CYC1t-TRP1<br>erg6Δ::TDH3p-S24R1-PGK1t-URA3<br>erg4Δ::PGK1p-Scer-are1 G595D-CYC1t-LEU2<br>TDH3p-tHMG1 INT59 :: HSP26p-*U. maydis*-ERG2-TDH3t-NAT$^R$ | Targeted insertion construct at INT59 locus |
| | erg5Δ::PGK1p-S24R2-CYC1t-TRP1<br>erg6Δ::TDH3p-S24R1-PGK1t-URA3<br>erg4Δ::PGK1p-Scer-are1 G595D-CYC1t-LEU2<br>TDH3p-tHMG1 INT59 :: HSP26p-*C. albicans*-ERG2-TDH3t-NAT$^R$ | Targeted insertion construct at INT59 locus |
| | erg5Δ::PGK1p-S24R2-CYC1t-TRP1<br>erg6Δ::TDH3p-S24R1-PGK1t-URA3<br>erg4Δ::PGK1p-Scer-are1 G595D-CYC1t-LEU2<br>TDH3p-tHMG1 INT59::HSP26p-*S. pombe*-ERG2-TDH3t-NAT$^R$ | Targeted insertion construct at INT59 locus |

TABLE 2 plasmids used for cloning of ERG2 homologs.

| Plasmid | Backbone | Insert | Oligos or source |
|---|---|---|---|
| pMB7677 | pMB7621 | *S. cerevisiae*-ERG2 | Synthesized fragment |
| pMB7732 | pMB7621 | *U. maydis*-ERG2 | Synthesized fragment |
| pMB7683 | pMB7621 | *C. albicans*-ERG2 | Synthesized fragment |
| pMB7681 | pMB7621 | *S. pombe*-ERG2 | Synthesized fragment |

Example 2: Cloning of Various ERG2 Homologs into *S. cerevisiae* Y2159

All ERG2 cassettes were constructed as follows. Open reading frames were codon-optimized based on the deduced amino acid sequence and synthesized with 5'-XbaI (TCTAGAACAAAatg . . . ) sites and 3'-PstI sites). These were cloned by inserting XbaII-PstII-digested ERG2 fragments into XbaII-PstII-digested pMB7621, which allows targeting to the intergenic locus INT59 on chromosome XI between the SRP40 and PTR2 genes (ca. position 615,000).

Besides *S. cerevisiae* ERG2 (SEQ ID NO: 1; plasmid pMB7677), the genes synthesized comprise ERG2 homologues (codon-optimized) from *Ustilago maydis* (SEQ ID NO: 9; plasmid pMB7732), *Candida albicans* (SEQ ID NO:

10; plasmid pMB7683), and *Schizosaccharomyces pombe* (SEQ ID NO:11; plasmid pMB7681), see sequence listing.

To test the impact of the different ERG2 genes in 7-DHC production, strain Y2159 was transformed with four different SfiI-generated fragments, representing one of the four species detailed above, at the INT59 locus using nourseothricin resistance (NatR) as a selectable marker, and the strong constitutive HSP26 promoter as a controlling element.

Transformants were selected on YPD agar with 200 mg/L nourseothricin after 3 days at 30° C. Strains resulting from these transformations are listed in Table 1 above. These strains were subsequently assayed for their 7-DHC productivity and overall 7-DHC sterol purity as described below.

Example 3: HPLC Analysis of Sterols from Transformed Strains

Strains were cultivated as follows. Strains to be tested were initially plated onto YPD agar and incubated for 48 hours at 30° C. Two milliliters YPD pre-cultures were inoculated from these plates and grown on a roller wheel for 24 hours at 30° C. In a 24-well microtiter plate, 0.8 mL of YPD+10 g/L ethanol were inoculated from the preculture to a final $OD_{600}$ of 0.5. Microtiter plates were grown at 30° C. in a humidified environment and shaking at 800 rpm on a shaker with an orbit of 3 mm. At 24 and 48 hours post-inoculation, 16 μl ethanol was added to each well as a feed. At 72 hours post-inoculation the cells were sampled for sterol content.

Sterols from the cultures were extracted and assayed as follows. Eighty microliters of whole broth were pipetted into a 2-mL Precellys tube with glass beads. Eight hundred microliters of saponification solution (5% KOH in ethanol) was added, and samples were placed into a Precellys 24 Homogenizer and agitated at 6500 rpm for 3 cycles at 15 seconds per cycle. Sixty microliters of glacial acetic acid were then added and the tubes were centrifuged for 1 minute at top speed. The supernatant was assayed via HPLC for sterol content. The results are shown in Table 3, 4 and 5.

TABLE 3 ratios of 7-DHC to zymosterol in control and strains carrying ERG2 homologs.

| Strain | Ratio 7-DHC to zymosterol |
| --- | --- |
| SC2159 - parent | 22.9 |
| U. maydis ERG2 | 28.4 |

TABLE 3 ratios of 7-DHC to cholesta-8-enol in control and strains carrying ERG2 homologs.

| Strain | Ratio 7-DHC to Cholesta-8-enol |
| --- | --- |
| SC2159 - parent | 8.7 |
| U. maydis ERG2 | 38.1 |
| C. albicans ERG2 | 21.9 |
| S. pombe ERG2 | 21 |
| S. cerevisiae ERG2 | 24.4 |

TABLE 4 ratios of 7-DHC to mix of lanosterol and lathosterol in control and strains carrying ERG2 homologs.

| Strain | Ratio 7-DHC to lanosterol/lathosterol |
| --- | --- |
| SC2159 - parent | 12.9 |
| U. maydis ERG2 | 17.1 |
| S. pombe ERG2 | 13.6 |

Example 4: Construction of Y2159

Wild-type *S. cerevisiae* ARE1 was synthesized by DNA2.0, incorporating an XbaI site at the 5' end (TCTAGAACAAAatg . . . ) and a PstI site at the 3'end. This was cloned into an erg4Δ::Hyg$^R$ deletion plasmid using unique XbaI and PstI sites. LEU2 was subsequently used to replace the HygR moiety via a KpnI-AgeI cloning. The result was plasmid pHyD459.

*S. cerevisiae* ARE1 mutant variant pMB7584 (F592L) was generated by ligating a BsrGI-BsaI-cleaved PCR product generated from ARE1 (oligos according to SEQ ID NO:16 & 17) with a double-stranded oligo derived by annealing SEQ ID NO:19 and 20 into BsrGI-PstI-cleaved pHyD459. Similarly, *S. cerevisiae* ARE1 mutant variant pMB7585 (G595D) was generated by ligating a BsrGI-BsaI-cleaved PCR product generated from ARE1 (oligos according to SEQ ID NO:16 & 18) with a double-stranded oligo derived by annealing SEQ ID NO:21 and 22 into BsrGI-PstI-cleaved pHyD459. The oligos as well as further sequences used herein are listed in Table 5.

TABLE 5 plasmids used for construction of ARE mutations. "Scer" means *Saccharomyces cerevisiae*.

| Plasmid | Backbone | Insert | Oligos or source | SEQ ID NO |
| --- | --- | --- | --- | --- |
| pHyD459 | pHyD445 | Scer-ARE1 | LEU2 insertion | |
| pMB7584 | pHyD459 | Scer-are1 F592L | MO10013 & MO10014, | 16 & 17 |
| | | | MO10016 & MO10017 | 19 & 20 |
| pMB7585 | pHyD459 | Scer-are1 G595D | MO10013 & MO10015 | 16 & 18 |

The invention claimed is:

1. A cholesterol-producing yeast cell expressing a heterologous enzyme having C8-sterol isomerase activity, said yeast cell producing a sterol mix comprising at least 80% 7-dehydrocholesterol (7-DHC), wherein said heterologous enzyme comprises an amino acid sequence having at least 95% identity to SEQ ID NO:6.

2. The cholesterol-producing yeast cell according to claim 1, wherein the sterol mix comprises cholesta-8-enol at a ratio of 7-DHC to cholesta-8-enol that is increased by at least 2-fold compared to the ratio of 7-DHC to cholesta-8-enol in a sterol mix produced by a reference yeast cell that does not express the heterologous enzyme having C8-sterol isomerase activity.

3. The cholesterol-producing yeast cell according to claim 1, said heterologous enzyme is an *Ustilago maydis* C8-sterol isomerase.

4. The cholesterol-producing yeast cell according to claim 1 in which ERG5 and ERG6 are inactivated.

5. The cholesterol-producing yeast cell according to claim 1, wherein the yeast cell expresses a heterologous enzyme selected from EC 1.3.1.72 having sterol Δ24-reductase activity.

6. The cholesterol-producing yeast cell according to claim 1, wherein the yeast cell expresses a heterologous enzyme having C5-desaturase activity.

7. A process for producing 7-DHC, comprising cultivating said cholesterol-producing yeast cell according to claim 1.

8. The process according to claim 7, further comprising converting the 7-DHC into vitamin D3.

9. The process according to claim 7, further comprising converting the 7-DHC into 25-hydroxyvitamin D3.

10. A process for reducing the amount of cholesta-8-enol in a sterol mix produced by a yeast cell, said process comprising expressing a heterologous enzyme having C8-sterol isomerase activity in the yeast cell, said enzyme comprising an amino acid sequence having at least 95% identity to SEQ ID NO:6.

11. A process for the production of a sterol mix in a yeast cell comprising:

(a) inactivating ERG5 and ERG6,
(b) expressing of a heterologous enzyme selected from EC 1.3.1.72 having sterol Δ24-reductase activity on cholesta-7,24-dienol, zymosterol or trienol,
(c) expressing a heterologous enzyme having C8-sterol isomerase activity, said enzyme comprising an amino acid sequence having at least 95% identity to SEQ ID NO:6, and
(d) cultivating said yeast cell under;
wherein the ratio of 7-DHC to cholesta-8-enol present in the sterol mix is more than 8.7.

* * * * *

SEQUENCE LISTING

<160> NUMBER OF SEQ ID NOS: 22

<210> SEQ ID NO 1
<211> LENGTH: 669
<212> TYPE: DNA
<213> ORGANISM: Saccharomyces cerevisiae

<400> SEQUENCE: 1

| | | | | | | |
|---|---|---|---|---|---|---|
| atgaagtttt | tcccactcct | tttgttgatt | ggtgttgtag | gctacattat | gaacgtattg | 60 |
| ttcactacct | ggttgccaac | caattacatg | ttcgatccaa | aaactttgaa | cgaaatatgt | 120 |
| aactcggtga | ttagcaaaca | caacgcagca | gaaggtttat | ccactgaaga | cctgttacag | 180 |
| gatgtcagag | acgcacttgc | ctctcattac | ggggacgaat | acatcaacag | gtacgtcaaa | 240 |
| gaagaatggg | tcttcaacaa | tgctggtggt | gcgatgggcc | aaatgatcat | cctacacgct | 300 |
| tccgtatccg | agtacttaat | tctattcgga | accgctgttg | gtactgaagg | cacacaggt | 360 |
| gttcactttg | ctgacgacta | ttttaccatc | ttacatggta | cgcaaatcgc | agcattgcca | 420 |
| tatgccactg | aagccgaagt | ttacactcct | ggtatgactc | atcacttgaa | gaagggatac | 480 |
| gccaagcaat | acagcatgcc | aggtggttcc | tttgcccttg | aattggctca | aggctggatt | 540 |
| ccatgtatgt | tgccattcgg | gtttttggac | actttctcca | gtactcttga | tttatacact | 600 |
| ctatatagaa | ctgtctacct | gactgccagg | gacatgggta | agaacttgtt | gcaaaacaaa | 660 |
| aagttctaa | | | | | | 669 |

<210> SEQ ID NO 2
<211> LENGTH: 726
<212> TYPE: DNA
<213> ORGANISM: Ustilago maydis

<400> SEQUENCE: 2

| | | | | | | |
|---|---|---|---|---|---|---|
| atggcatcgc | atagaccacg | cagcaacaag | gctgccaatg | gtgcttcgac | ttcacccaaa | 60 |
| cgcagctgga | taattgtctc | agctgcgctc | gttggcttct | gcgctctcat | cgccgctctc | 120 |
| gattcgatcc | gatccagctt | ctacatcttt | gaccacaagg | caatctacaa | gatcgcatcg | 180 |
| actgcggtcg | ccaaccatcc | aggcaatgcg | acggccatct | tgatgatgt | cctcgacaac | 240 |
| cttcgtgccg | accccaagct | cgcgccttac | atcaacaaga | tcatttcag | cgacgagtca | 300 |
| gaatggatgt | tcaacaatgc | cggtggtgct | atgggtagca | tgttcatcat | tcatgcttcc | 360 |
| gtcaccgagt | acctgatctt | ctttggcact | cccgtcggaa | ccgagggtca | cactggtcgt | 420 |
| cacacagccg | atgactactt | caacatcctt | accggtaacc | aatacgcttt | cccagctggt | 480 |
| gcgctcaagg | cggagcacta | ccctgccgga | tcagtgcacc | atcttcgccg | cggaacggtc | 540 |
| aagcagtaca | tgatgcctga | agacggctgc | tgggcgctcg | agcttgctca | gggctggatc | 600 |
| ccacccatgc | ttcccttggg | tctcgccgat | gtgctcagct | cgacgctcga | cctgcccacc | 660 |
| tttggtatca | ctgtctggat | cactgcacga | gaaatggttg | gcaatctgct | catcggcaag | 720 |
| ttttga | | | | | | 726 |

<210> SEQ ID NO 3
<211> LENGTH: 654
<212> TYPE: DNA
<213> ORGANISM: Candida albicans

<400> SEQUENCE: 3

| | | | | | | |
|---|---|---|---|---|---|---|
| atgaagttat | tattagtagg | aattattcca | attgcattat | atgctatttt | caattattta | 60 |
| ttttatactt | ggttacctac | caattattta | tttgataaac | aagtattaca | agaattagtt | 120 |

```
caagaaacat taaaggatca tccagatggt aatgccacgg ccattatgat tgatttgact    180
ccaaaaattc aaagaaata tcctaaaatc attaatgatt taaattttga tgattgggtt    240
tataataatg ctggtggtgc catgggtaca atgtttattt tacatgcatc aatttctgaa    300
tatttgattt ttttcggtac agcaattggg actgaaggtc atactggagt tcattttgct    360
gatgattatt tcacaatttt aactggtgaa caaagagcag cttatcctgg tgcattgatt    420
cccgaagttt atttaccagg tgatcaacac catttaccaa aggtcatgt taaacaatat     480 gctatgcccg tgaatcatt tgccttagaa ttggctcaag gctggattcc agcaatgtta    540
ccatttggat ttttgatac tttgacttca acaatggatt tctatacttt ttacttgact    600
gcttattaca ctggtaaaga tatgatcaag aatttattaa ttgggaaatt ctaa          654
```

<210> SEQ ID NO 4
<211> LENGTH: 660
<212> TYPE: DNA
<213> ORGANISM: Schizosaccharomyces pombe

<400> SEQUENCE: 4

```
atgaaattga caaagttttt aactgtgttc attccttta ttgctggatt gatttattat      60
atacaaaaat atcatcttcg ttccttctat caatttgatc cagcaaagtt gcaggagcta    120
tctaagcagt ctattgcttt atacgcaaat gataccaaag ctcttcttta cgacttgagc    180
gacagactcg ttgctgaata cggagactta attactcctg tgaatcaaga tgaatgggtt    240
cacaacaatg ctggtggtgc tatgggtaca atgtttatct tgcatgcttc cttttctgag    300
tacttgattt tctttggcac gcctatcggc accgagggac attctggtgt tcatatggct    360
gacgattatt tcactatttt acgtggccgt caacttgctg cttctgctaa tgaccttgag    420
gctcgtgttt atcttcctgg tgaccaacat gttcatcctt ggggtcacac tgctcagtat    480
agcatgccgt ctggtgaacc ttgttttgct cttgaactag ctcaaggatg gattgtatca    540
atgcttccct ttggatttat ggatggttta ttctccacca ttgatttcgg aactttatac    600
aaaaccgttt atttcactgc gggaaggatg ttgaaaagtg ttttaatggg aaaattctaa    660
```

<210> SEQ ID NO 5
<211> LENGTH: 222
<212> TYPE: PRT
<213> ORGANISM: Saccharomyces cerevisiae

<400> SEQUENCE: 5

```
Met Lys Phe Phe Pro Leu Leu Leu Ile Gly Val Val Gly Tyr Ile
1               5                   10                  15

Met Asn Val Leu Phe Thr Thr Trp Leu Pro Thr Asn Tyr Met Phe Asp
                20                  25                  30

Pro Lys Thr Leu Asn Glu Ile Cys Asn Ser Val Ile Ser Lys His Asn
            35                  40                  45

Ala Ala Glu Gly Leu Ser Thr Glu Asp Leu Leu Gln Asp Val Arg Asp
        50                  55                  60

Ala Leu Ala Ser His Tyr Gly Asp Glu Tyr Ile Asn Arg Tyr Val Lys
65                  70                  75                  80

Glu Glu Trp Val Phe Asn Asn Ala Gly Ala Met Gly Gln Met Ile
                85                  90                  95

Ile Leu His Ala Ser Val Ser Glu Tyr Leu Ile Leu Phe Gly Thr Ala
            100                 105                 110

Val Gly Thr Glu Gly His Thr Gly Val His Phe Ala Asp Asp Tyr Phe
```

```
            115                 120                 125
Thr Ile Leu His Gly Thr Gln Ile Ala Ala Leu Pro Tyr Ala Thr Glu
    130                 135                 140

Ala Glu Val Tyr Thr Pro Gly Met Thr His His Leu Lys Lys Gly Tyr
145                 150                 155                 160

Ala Lys Gln Tyr Ser Met Pro Gly Gly Ser Phe Ala Leu Glu Leu Ala
                165                 170                 175

Gln Gly Trp Ile Pro Cys Met Leu Pro Phe Gly Phe Leu Asp Thr Phe
            180                 185                 190

Ser Ser Thr Leu Asp Leu Tyr Thr Leu Tyr Arg Thr Val Tyr Leu Thr
        195                 200                 205

Ala Arg Asp Met Gly Lys Asn Leu Leu Gln Asn Lys Lys Phe
    210                 215                 220
```

<210> SEQ ID NO 6
<211> LENGTH: 241
<212> TYPE: PRT
<213> ORGANISM: Ustilago maydis

<400> SEQUENCE: 6

```
Met Ala Ser His Arg Pro Arg Ser Asn Lys Ala Asn Gly Ala Ser
1               5                   10                  15

Thr Ser Pro Lys Arg Ser Trp Ile Ile Val Ser Ala Ala Leu Val Gly
            20                  25                  30

Phe Cys Ala Leu Ile Ala Ala Leu Asp Ser Ile Arg Ser Ser Phe Tyr
            35                  40                  45

Ile Phe Asp His Lys Ala Ile Tyr Lys Ile Ala Ser Thr Ala Val Ala
    50                  55                  60

Asn His Pro Gly Asn Ala Thr Ala Ile Phe Asp Asp Val Leu Asp Asn
65                  70                  75                  80

Leu Arg Ala Asp Pro Lys Leu Ala Pro Tyr Ile Asn Lys Asn His Phe
            85                  90                  95

Ser Asp Glu Ser Glu Trp Met Phe Asn Asn Ala Gly Gly Ala Met Gly
                100                 105                 110

Ser Met Phe Ile Ile His Ala Ser Val Thr Glu Tyr Leu Ile Phe Phe
            115                 120                 125

Gly Thr Pro Val Gly Thr Glu Gly His Thr Gly Arg His Thr Ala Asp
    130                 135                 140

Asp Tyr Phe Asn Ile Leu Thr Gly Asn Gln Tyr Ala Phe Pro Ala Gly
145                 150                 155                 160

Ala Leu Lys Ala Glu His Tyr Pro Ala Gly Ser Val His His Leu Arg
                165                 170                 175

Arg Gly Thr Val Lys Gln Tyr Met Met Pro Glu Asp Gly Cys Trp Ala
            180                 185                 190

Leu Glu Leu Ala Gln Gly Trp Ile Pro Pro Met Leu Pro Phe Gly Leu
        195                 200                 205

Ala Asp Val Leu Ser Ser Thr Leu Asp Leu Pro Thr Phe Gly Ile Thr
    210                 215                 220

Val Trp Ile Thr Ala Arg Glu Met Val Gly Asn Leu Leu Ile Gly Lys
225                 230                 235                 240

Phe
```

<210> SEQ ID NO 7
<211> LENGTH: 217
<212> TYPE: PRT

<213> ORGANISM: Candida albicans

<400> SEQUENCE: 7

Met Lys Leu Leu Leu Val Gly Ile Ile Pro Ile Ala Leu Tyr Ala Ile
1               5                   10                  15

Phe Asn Tyr Leu Phe Tyr Thr Trp Leu Pro Thr Asn Tyr Leu Phe Asp
            20                  25                  30

Lys Gln Val Leu Gln Glu Leu Val Gln Glu Thr Leu Lys Asp His Pro
        35                  40                  45

Asp Gly Asn Ala Thr Ala Ile Met Ile Asp Leu Thr Pro Lys Ile Gln
    50                  55                  60

Lys Lys Tyr Pro Lys Ile Ile Asn Asp Leu Asn Phe Asp Asp Trp Val
65                  70                  75                  80

Tyr Asn Asn Ala Gly Gly Ala Met Gly Thr Met Phe Ile Leu His Ala
                85                  90                  95

Ser Ile Ser Glu Tyr Leu Ile Phe Phe Gly Thr Ala Ile Gly Thr Glu
            100                 105                 110

Gly His Thr Gly Val His Phe Ala Asp Asp Tyr Phe Thr Ile Leu Thr
        115                 120                 125

Gly Glu Gln Arg Ala Ala Tyr Pro Gly Ala Leu Ile Pro Glu Val Tyr
    130                 135                 140

Leu Pro Gly Asp Gln His His Leu Pro Lys Gly His Val Lys Gln Tyr
145                 150                 155                 160

Ala Met Pro Gly Glu Ser Phe Ala Leu Glu Leu Ala Gln Gly Trp Ile
                165                 170                 175

Pro Ala Met Leu Pro Phe Gly Phe Leu Asp Thr Leu Thr Ser Thr Met
            180                 185                 190

Asp Phe Tyr Thr Phe Tyr Leu Thr Ala Tyr Tyr Thr Gly Lys Asp Met
        195                 200                 205

Ile Lys Asn Leu Leu Ile Gly Lys Phe
    210                 215

<210> SEQ ID NO 8
<211> LENGTH: 219
<212> TYPE: PRT
<213> ORGANISM: Schizosaccharomyces pombe

<400> SEQUENCE: 8

Met Lys Leu Thr Lys Phe Leu Thr Val Phe Ile Pro Phe Ile Ala Gly
1               5                   10                  15

Leu Ile Tyr Tyr Ile Gln Lys Tyr His Leu Arg Ser Phe Tyr Gln Phe
            20                  25                  30

Asp Pro Ala Lys Leu Gln Glu Leu Ser Lys Gln Ser Ile Ala Leu Tyr
        35                  40                  45

Ala Asn Asp Thr Lys Ala Leu Leu Tyr Asp Leu Ser Asp Arg Leu Val
    50                  55                  60

Ala Glu Tyr Gly Asp Leu Ile Thr Pro Val Asn Gln Asp Glu Trp Val
65                  70                  75                  80

His Asn Asn Ala Gly Gly Ala Met Gly Thr Met Phe Ile Leu His Ala
                85                  90                  95

Ser Phe Ser Glu Tyr Leu Ile Phe Phe Gly Thr Pro Ile Gly Thr Glu
            100                 105                 110

Gly His Ser Gly Val His Met Ala Asp Asp Tyr Phe Thr Ile Leu Arg
        115                 120                 125

Gly Arg Gln Leu Ala Ala Ser Ala Asn Asp Leu Glu Ala Arg Val Tyr

|  | 130 |  |  |  | 135 |  |  |  | 140 |  |  |
|---|---|---|---|---|---|---|---|---|---|---|---|

Leu Pro Gly Asp Gln His Val His Pro Trp Gly His Thr Ala Gln Tyr
145                 150                 155                 160

Ser Met Pro Ser Gly Glu Pro Cys Phe Ala Leu Glu Leu Ala Gln Gly
                165                 170                 175

Trp Ile Val Ser Met Leu Pro Phe Gly Phe Met Asp Gly Leu Phe Ser
            180                 185                 190

Thr Ile Asp Phe Gly Thr Leu Tyr Lys Thr Val Tyr Phe Thr Ala Gly
        195                 200                 205

Arg Met Leu Lys Ser Val Leu Met Gly Lys Phe
    210                 215

<210> SEQ ID NO 9
<211> LENGTH: 726
<212> TYPE: DNA
<213> ORGANISM: Artificial Sequence
<220> FEATURE:
<223> OTHER INFORMATION: S. cerevisiae codon-optimized U. maydis ERG2

<400> SEQUENCE: 9

```
atggcttccc atagaccacg ttccaacaag gccgctaatg gtgcttccac ttctccaaag    60
cgttcctgga ttattgtctc tgctgccttg gtcggtttct gcgctttgat cgccgctttg   120
gactccatcc gttcctcctt ctacatcttt gaccacaagg ctatctacaa gatcgcttcc   180
actgccgtcg ccaaccatcc aggtaacgcc accgccatct tgatgatgt cttggacaac   240
ttgagagccg accctaagtt ggccccatac atcaacaaga tcatttctc cgacgaatcc   300
gaatggatgt tcaataacgc cggtggtgct atgggttcca tgttcatcat tcatgcttcc   360
gtcaccgaat acttgatctt cttcggtact cctgtcggta ctgaaggtca cactggtcgt   420
cacaccgctg atgactactt caacatcttg actggtaacc aatacgcttt cccagctggt   480
gccttgaagg ccgaacacta cccagccggt tctgtccacc atttgcgtag aggtactgtc   540
aagcaataca tgatgcctga agacggttgc tgggccttgg aattggccca aggttggatt   600
cctccaatgt tgcctttcgg tttggccgac gtcttgtcct ccaccttgga cttgcctacc   660
tttggtatca ctgtctggat cactgctcgt gaaatggttg gtaacttgtt gatcggtaag   720
ttctaa                                                              726
```

<210> SEQ ID NO 10
<211> LENGTH: 654
<212> TYPE: DNA
<213> ORGANISM: Artificial Sequence
<220> FEATURE:
<223> OTHER INFORMATION: S. cerevisiae codon-optimized C. albicans ERG2

<400> SEQUENCE: 10

```
atgaaattgt tattggttgg tattattcca attgctttat acgctatttt caactactta    60
ttctatactt ggttaccaac taactatttg tttgataaac aagttttaca agaattagtt   120
caagaaactt taaaggatca tccagatggt aacgctaccg ccattatgat tgatttgact   180
ccaaaaattc aaaagaagta tccaaaaatc attaatgatt taaactttga tgattgggtt   240
tacaataacg ctggtggtgc catgggtact atgtttattt tacatgcttc tatttctgaa   300
tatttgattt ctttggtac tgctatcggt actgaaggtc atactggtgt tcattttgct   360
gatgattatt tcactatttt aactggtgaa caaagagctg cttatccagg tgctttgatc   420
cctgaagttt atttgccagg tgatcaacac catttaccaa aaggtcatgt taaacaatat   480
```

-continued

```
gctatgccag gtgaatcttt tgctttggaa ttggctcaag gttggattcc agctatgtta    540
ccatttggtt ttttggatac tttgacttct actatggatt tctatacttt ttacttgact    600
gcttattaca ctggtaaaga tatgatcaag aatttgttaa tcggtaaatt ctaa          654
```

<210> SEQ ID NO 11
<211> LENGTH: 660
<212> TYPE: DNA
<213> ORGANISM: Artificial Sequence
<220> FEATURE:
<223> OTHER INFORMATION: S. cerevisiae codon-optimized Sch. pombe ERG2

<400> SEQUENCE: 11

```
atgaaattga ctaagttttt gactgtcttc attccattta ttgctggttt gatttactat     60
attcaaaagt atcatttgcg ttccttctat caatttgatc cagctaagtt gcaagaattg    120
tccaagcaat ccattgcttt atacgctaat gatactaagg ctttgttgta cgacttgtcc    180
gacagattgg tcgctgaata cggtgactta attactcctg tcaatcaaga tgaatgggtt    240
cacaataacg ctggtggtgc tatgggtact atgtttatct tgcatgcttc cttttccgaa    300
tacttgattt tcttcggtac tcctatcggt actgaaggtc attctggtgt tcatatggct    360
gacgattatt tcactatttt cgtggtcgt caattggctg cttctgctaa tgacttggaa    420
gctcgtgttt atttgcctgg tgaccaacat gttcatcctt ggggtcacac tgcccaatat    480
tccatgcctt ccggtgaacc ttgttttgct ttggaattgg ctcaaggttg gattgtttct    540
atgttgcctt tcggtttat ggatggttta ttctccacca ttgatttcgg tactttatac    600
aaaaccgttt atttcactgc cggtcgtatg ttgaaatctg ttttaatggg taaattctaa    660
```

<210> SEQ ID NO 12
<211> LENGTH: 610
<212> TYPE: PRT
<213> ORGANISM: Saccharomyces cerevisiae

<400> SEQUENCE: 12

```
Met Thr Glu Thr Lys Asp Leu Leu Gln Asp Glu Glu Phe Leu Lys Ile
1               5                   10                  15

Arg Arg Leu Asn Ser Ala Glu Ala Asn Lys Arg His Ser Val Thr Tyr
            20                  25                  30

Asp Asn Val Ile Leu Pro Gln Glu Ser Met Glu Val Ser Pro Arg Ser
        35                  40                  45

Ser Thr Thr Ser Leu Val Glu Pro Val Glu Ser Thr Glu Gly Val Glu
    50                  55                  60

Ser Thr Glu Ala Glu Arg Val Ala Gly Lys Gln Glu Gln Glu Glu Glu
65                  70                  75                  80

Tyr Pro Val Asp Ala His Met Gln Lys Tyr Leu Ser His Leu Lys Ser
                85                  90                  95

Lys Ser Arg Ser Arg Phe His Arg Lys Asp Ala Ser Lys Tyr Val Ser
            100                 105                 110

Phe Phe Gly Asp Val Ser Phe Asp Pro Arg Pro Thr Leu Leu Asp Ser
        115                 120                 125

Ala Ile Asn Val Pro Phe Gln Thr Thr Phe Lys Gly Pro Val Leu Glu
    130                 135                 140

Lys Gln Leu Lys Asn Leu Gln Leu Thr Lys Thr Lys Thr Lys Ala Thr
145                 150                 155                 160

Val Lys Thr Thr Val Lys Thr Thr Glu Lys Thr Asp Lys Ala Asp Ala
                165                 170                 175
```

-continued

Pro Pro Gly Glu Lys Leu Glu Ser Asn Phe Ser Gly Ile Tyr Val Phe
            180                 185                 190

Ala Trp Met Phe Leu Gly Trp Ile Ala Ile Arg Cys Cys Thr Asp Tyr
        195                 200                 205

Tyr Ala Ser Tyr Gly Ser Ala Trp Asn Lys Leu Glu Ile Val Gln Tyr
    210                 215                 220

Met Thr Thr Asp Leu Phe Thr Ile Ala Met Leu Asp Leu Ala Met Phe
225                 230                 235                 240

Leu Cys Thr Phe Phe Val Val Phe Val His Trp Leu Val Lys Lys Arg
                245                 250                 255

Ile Ile Asn Trp Lys Trp Thr Gly Phe Val Ala Val Ser Ile Phe Glu
            260                 265                 270

Leu Ala Phe Ile Pro Val Thr Phe Pro Ile Tyr Val Tyr Tyr Phe Asp
        275                 280                 285

Phe Asn Trp Val Thr Arg Ile Phe Leu Phe Leu His Ser Val Val Phe
    290                 295                 300

Val Met Lys Ser His Ser Phe Ala Phe Tyr Asn Gly Tyr Leu Trp Asp
305                 310                 315                 320

Ile Lys Gln Glu Leu Glu Tyr Ser Ser Lys Gln Leu Gln Lys Tyr Lys
                325                 330                 335

Glu Ser Leu Ser Pro Glu Thr Arg Glu Ile Leu Gln Lys Ser Cys Asp
            340                 345                 350

Phe Cys Leu Phe Glu Leu Asn Tyr Gln Thr Lys Asp Asn Asp Phe Pro
        355                 360                 365

Asn Asn Ile Ser Cys Ser Asn Phe Phe Met Phe Cys Leu Phe Pro Val
370                 375                 380

Leu Val Tyr Gln Ile Asn Tyr Pro Arg Thr Ser Arg Ile Arg Trp Arg
385                 390                 395                 400

Tyr Val Leu Glu Lys Val Cys Ala Ile Ile Gly Thr Ile Phe Leu Met
                405                 410                 415

Met Val Thr Ala Gln Phe Phe Met His Pro Val Ala Met Arg Cys Ile
            420                 425                 430

Gln Phe His Asn Thr Pro Thr Phe Gly Gly Trp Ile Pro Ala Thr Gln
        435                 440                 445

Glu Trp Phe His Leu Leu Phe Asp Met Ile Pro Gly Phe Thr Val Leu
    450                 455                 460

Tyr Met Leu Thr Phe Tyr Met Ile Trp Asp Ala Leu Leu Asn Cys Val
465                 470                 475                 480

Ala Glu Leu Thr Arg Phe Ala Asp Arg Tyr Phe Tyr Gly Asp Trp Trp
                485                 490                 495

Asn Cys Val Ser Phe Glu Glu Phe Ser Arg Ile Trp Asn Val Pro Val
            500                 505                 510

His Lys Phe Leu Leu Arg His Val Tyr His Ser Ser Met Gly Ala Leu
        515                 520                 525

His Leu Ser Lys Ser Gln Ala Thr Leu Phe Thr Phe Phe Leu Ser Ala
    530                 535                 540

Val Phe His Glu Met Ala Met Phe Ala Ile Phe Arg Arg Val Arg Gly
545                 550                 555                 560

Tyr Leu Phe Met Phe Gln Leu Ser Gln Phe Val Trp Thr Ala Leu Ser
                565                 570                 575

Asn Thr Lys Phe Leu Arg Ala Arg Pro Gln Leu Ser Asn Val Val Phe
            580                 585                 590

Ser Phe Gly Val Cys Ser Gly Pro Ser Ile Ile Met Thr Leu Tyr Leu

Thr Leu
   610

<210> SEQ ID NO 13
<211> LENGTH: 1833
<212> TYPE: DNA
<213> ORGANISM: Saccharomyces cerevisiae

<400> SEQUENCE: 13

```
atgacggaga ctaaggattt gttgcaagac gaagagtttc ttaagatccg cagactcaat       60
tccgcagaag ccaacaaacg gcattcggtc acgtacgata acgtgatcct gccacaggag      120
tccatggagg tttcgccacg gtcgtctacc acgtcgctgg tggagccagt ggagtcgact      180
gaaggagtgg agtcgactga ggcggaacgt gtggcaggga agcaggagca ggaggaggag      240
taccctgtgg acgcccacat gcaaaagtac cttcacacc tgaagagcaa gtctcggtcg      300
aggttccacc gaaaggatgc tagcaagtat gtgtcgtttt tggggacgt gagttttgat      360
cctcgcccca cgctcctgga cagcgccatc aacgtgccct tccagacgac tttcaaaggt      420
ccggtgctgg agaaacagct caaaaattta cagttgacaa agaccaagac caaggccacg      480
gtgaagacta cggtgaagac tacggagaaa acggacaagg cagatgcccc cccaggagaa      540
aaactggagt cgaacttttc agggatctac gtgttcgcat ggatgttctt gggctggata      600
gccatcaggt gctgcacaga ttactatgcg tcgtacggca gtgcatggaa taagctggaa      660
atcgtgcagt acatgacaac ggacttgttc acgatcgcaa tgttggactt ggcaatgttc      720
ctgtgcactt tcttcgtggt tttcgtgcac tggctggtga aaaagcggat catcaactgg      780
aagtggactg ggtcgttgc agtgagcatc ttcgagttgg cttcatccc cgtgacgttc      840
cccattacg tctactactt tgatttcaac tgggtcacga aatcttcct gttcctgcac      900
tccgtggtgt ttgttatgaa gagccactcg tttgcctttt acaacgggta tctttgggac      960
ataaagcagg aactcgagta ctcttccaaa cagttgcaaa aatacaagga atctttgtcc     1020
ccagagaccc gcgagattct gcaaaaaagt gcgacttttt gcctttcga attgaactac     1080
cagaccaagg ataacgactt ccccaacaac atcagttgca gcaatttctt catgttctgt     1140
tgttccccg tcctcgtgta ccagatcaac tacccaagaa cgtcgcgcat cagatggagg     1200
tatgtgttgg agaaggtgtg cgccatcatt ggaccatct tcctcatgat ggtcacggca     1260
cagttcttca tgcacccggt ggccatgcgc tgtatccagt tccacaacac gcccaccttc     1320
ggcggctgga tccccgccac gcaagagtgg ttccacctgc tcttcgacat gattccgggc     1380
ttcactgttc tgtacatgct cacgttttac atgatatggg acgctttatt gaattgcgtg     1440
gcggagttga ccaggtttgc ggacagatat ttctacggcg actggtggaa ttgcgtttcg     1500
tttgaagagt ttagcagaat ctggaacgtc cccgttcaca aatttttact aagacacgtg     1560
taccacagct ccatgggcgc attgcatttg agcaagagcc aagctacatt atttactttt     1620
ttcttgagtg ccgtgttcca cgaaatggcc atgttcgcca ttttcagaag ggttagagga     1680
tatctgttca tgttccaact gtcgcagttt gtgtggactg ctttgagcaa caccaagttt     1740
ctacgggcaa gaccgcagtt gtccaacgtt gtctttcgt tggtgtctg ttcagggccc     1800
agtatcatta tgacgttgta cctgaccta tga                                  1833
```

<210> SEQ ID NO 14
<211> LENGTH: 384
<212> TYPE: PRT

<213> ORGANISM: Pichia pastoris

<400> SEQUENCE: 14

```
Met Asp Ile Ala Leu Glu Ile Leu Asp Thr Phe Val Phe Asp Lys Val
1               5                   10                  15

Tyr Ala Lys Leu Leu Pro Ile Ser Leu Val Gln His Leu Pro Asp Gly
            20                  25                  30

Tyr Leu Lys Thr Leu Gly His Leu Thr Gly Ala Asn Asn Thr Met Glu
        35                  40                  45

Ser Leu Phe Gly Ile Ala Pro Asn Val Asp Gln Ala Ser Lys Asn His
    50                  55                  60

Trp Leu Arg Thr Val Asn Asp Ser Ile Ala Leu Ala Arg Pro Gly Glu
65                  70                  75                  80

Arg Leu Val Tyr Gly Val Asn Ala Pro Leu His Phe Phe Asp Glu Thr
                85                  90                  95

Ala Tyr Thr Tyr Ala Ser Ile Leu Gly Arg Ser Asn Ile Ile Arg Gln
            100                 105                 110

Phe Thr Thr Leu Met Ile Leu Met Ile Leu Phe Gly Trp Gly Leu Tyr
        115                 120                 125

Leu Ser Val Ala Ser Phe Ser Tyr Tyr Phe Val Phe Asp Lys Ala Ile
    130                 135                 140

Phe Asn His Pro Arg Tyr Leu Lys Asn Gln Met Ser Leu Glu Ile His
145                 150                 155                 160

Gln Ala Leu Thr Ala Ile Pro Thr Met Val Leu Leu Thr Val Pro Trp
                165                 170                 175

Phe Leu Ile Glu Leu Arg Gly Tyr Ser Lys Leu Tyr Phe Asp Val Asn
            180                 185                 190

Glu Ser Thr Gly Gly Trp Lys Ala Ile Ile Trp Gln Ile Pro Cys Phe
        195                 200                 205

Ile Met Phe Thr Asp Cys Cys Ile Tyr Phe Ile His Arg Trp Leu His
    210                 215                 220

Trp Pro Ser Val Tyr Lys Arg Leu His Lys Pro His His Lys Trp Ile
225                 230                 235                 240

Val Cys Thr Pro Phe Ala Ser His Ala Phe His Pro Val Asp Gly Tyr
                245                 250                 255

Ala Gln Ser Leu Pro Tyr His Leu Tyr Gly Met Leu Phe Pro Leu His
            260                 265                 270

Lys Val Ser Tyr Leu Ile Leu Phe Gly Leu Val Asn Phe Trp Thr Val
        275                 280                 285

Met Ile His Asp Gly Glu Tyr Leu Ser Arg Asp Pro Ile Val Asn Gly
    290                 295                 300

Ala Ala Cys His Thr Val His His Leu Tyr Phe Asn Tyr Asn Tyr Gly
305                 310                 315                 320

Gln Phe Thr Thr Leu Trp Asp Arg Leu Gly Gly Ser Tyr Arg Met Pro
                325                 330                 335

Asp Lys Glu Leu Phe Asp Lys Asn Lys Lys Asp Val Lys Thr Trp
            340                 345                 350

Arg Ser Gln Val Lys Gln Ala Asp Ser Ile Arg Glu Asp Leu Glu Gly
        355                 360                 365

Lys Glu Asp Phe Arg Glu Tyr Gly Thr Glu Glu Lys Leu Lys Ser Thr
    370                 375                 380
```

<210> SEQ ID NO 15
<211> LENGTH: 1155

<212> TYPE: DNA
<213> ORGANISM: Pichia pastoris

<400> SEQUENCE: 15

```
atggacattg ctttggagat tctagacact tttgtctttg acaaagtcta tgcaaaacta      60
ctgcccattt ctctggtgca acatttgcca gatggctatt tgaagacttt gggacatttg     120
actggtgcca acaacaccat ggaatcactg ttcggaatag ctccaaacgt tgaccaagcg     180
tctaagaacc actggctgag aacagtgaat gactctattg ccttagcccg tcccggtgag     240
cgtctggtct acgtgtcaa cgctccttta cacttttttg acgaaacagc gtatacatac      300
gcatcgatct gggacgctc caatatcatt cgacaattca aactttgat gattctgatg       360
attcttttg ctggggttt gtatttatct gtggcttcat tttcatacta ctttgttttt       420
gataaagcca ttttcaatca cccaagatac ctcaaaaacc agatgtctct ggagatccat     480
caagcgttga ctgctatacc tacgatggtt ttgcttacag ttccatggtt tttgattgag     540
ttgcgtggat actctaaatt atactttgat gtaaatgagt ctactggagg atggaaggct     600
attatttggc aaattccttg cttcattatg tttaccgatt gttgtatcta ctttattcat     660
cgttggttgc actggccatc cgtgtataag cgtttgcaca gcctcacca caagtggatt      720
gtttgtacac cttttgctag tcatgccttc catccagttg atggttatgc acaatcacta     780
ccttaccatt tgtatggaat gttgtttcca ctacacaagg tgagctatct gatcttattt     840
gggcttgtga acttttggac tgttatgatc catgatggag aatacctgtc cagagaccct     900
atagtcaatg gagctgcttg tcatacagtg catcacctat acttcaacta caattacggc     960
cagttcacaa cactttggga ccgtcttggt ggatcataca gaatgccaga caaggaactc    1020
tttgataaga acaagaagaa agatgtaaag acatggcgtt cacaagtcaa gcaggccgat    1080
tcgataagag aagacttaga gggaaaagaa gatttccgtg agtatggaac tgaggaaaaa    1140
cttaaaagca catag                                                     1155
```

<210> SEQ ID NO 16
<211> LENGTH: 25
<212> TYPE: DNA
<213> ORGANISM: Artificial Sequence
<220> FEATURE:
<223> OTHER INFORMATION: primer

<400> SEQUENCE: 16

```
tgttctgtac atgctcacgt tttac                                            25
```

<210> SEQ ID NO 17
<211> LENGTH: 34
<212> TYPE: DNA
<213> ORGANISM: Artificial Sequence
<220> FEATURE:
<223> OTHER INFORMATION: primer

<400> SEQUENCE: 17

```
cacacggtct cacaagacaa cgttggacaa ctgc                                  34
```

<210> SEQ ID NO 18
<211> LENGTH: 37
<212> TYPE: DNA
<213> ORGANISM: Artificial Sequence
<220> FEATURE:
<223> OTHER INFORMATION: primer

<400> SEQUENCE: 18

```
cacacggtct caatcaaacg aaaagacaac gttggac                              37

<210> SEQ ID NO 19
<211> LENGTH: 66
<212> TYPE: DNA
<213> ORGANISM: Artificial Sequence
<220> FEATURE:
<223> OTHER INFORMATION: primer

<400> SEQUENCE: 19
cttgtcgttt ggtgtctgtt cagggcccag tatcattatg acgttgtacc tgaccttatg    60
actgca                                                                66

<210> SEQ ID NO 20
<211> LENGTH: 58
<212> TYPE: DNA
<213> ORGANISM: Artificial Sequence
<220> FEATURE:
<223> OTHER INFORMATION: primer

<400> SEQUENCE: 20
gtcataaggt caggtacaac gtcataatga tactgggccc tgaacagaca ccaaacga      58

<210> SEQ ID NO 21
<211> LENGTH: 57
<212> TYPE: DNA
<213> ORGANISM: Artificial Sequence
<220> FEATURE:
<223> OTHER INFORMATION: primer

<400> SEQUENCE: 21
tgatgtctgt tcagggccca gtatcattat gacgttgtac ctgaccttat gactgca       57

<210> SEQ ID NO 22
<211> LENGTH: 49
<212> TYPE: DNA
<213> ORGANISM: Artificial Sequence
<220> FEATURE:
<223> OTHER INFORMATION: primer

<400> SEQUENCE: 22
gtcataaggt caggtacaac gtcataatga tactgggccc tgaacagac               49
```